United States Patent [19]
Guthrie et al.

[11] Patent Number: 5,266,323
[45] Date of Patent: Nov. 30, 1993

[54] DEGRADABLE ARTICLES AND METHODS OF USING SUCH ARTICLES AS DEGRADABLE BAIT

[75] Inventors: James L. Guthrie, Ashton; Narendar P. Luthra, Columbia; Clifton L. Kehr, Silver Spring; Darwin S. Bull, Baltimore, all of Md.

[73] Assignee: Hampshire Chemical Corp., Lexington, Mass.

[21] Appl. No.: 705,276

[22] Filed: May 24, 1991

[51] Int. Cl.⁵ ............................................. A01N 25/08
[52] U.S. Cl. ..................................... 424/410; 424/84; 424/78.17; 43/42.06; 523/124
[58] Field of Search ................ 424/84, 421, 618, 724; 514/63

[56] References Cited

U.S. PATENT DOCUMENTS

| | | | |
|---|---|---|---|
| 135,113 | 1/1873 | Goodman | 424/84 |
| 3,410,689 | 11/1968 | Nathan | 99/3 |
| 3,684,519 | 8/1972 | Combs | 99/3 |
| 4,132,839 | 1/1979 | Marans et al. | 521/159 |
| 4,245,420 | 1/1981 | Carr | 43/42.06 |
| 4,463,018 | 7/1984 | Carr | 426/1 |
| 4,666,717 | 5/1987 | Smith et al. | 426/1 |
| 4,666,767 | 5/1987 | Von Kohorn et al. | 428/304.4 |
| 4,731,247 | 5/1988 | Wolford et al. | 426/1 |
| 4,921,703 | 5/1990 | Higuchi et al. | 424/419 |
| 4,983,389 | 1/1991 | Levy | 424/404 |

FOREIGN PATENT DOCUMENTS

| | | |
|---|---|---|
| 0295055 | 12/1988 | European Pat. Off. . |
| 0446156 | 9/1991 | European Pat. Off. . |
| 8701307 | 6/1987 | PCT Int'l Appl. . |

OTHER PUBLICATIONS

Toshiaki J. Hara, Developments in Aquaculture and Fishieries Science, 8, "Chemoreception in Fishes". Elsevier Scientific Publishing Co., 1982.

*Primary Examiner*—Paul R. Michl
*Assistant Examiner*—Neil Levy
*Attorney, Agent, or Firm*—Nields & Lemack

[57] ABSTRACT

A degradable article comprising a polyurethane polymer gel or foam whose polymer structure contains hydrolytically unstable ester linkages and various additives. The article can be constructed so that some of the additives are released from the article at a sustained rate. In a preferred embodiment the additives are sensory stimulants for marine or aquatic organisms and the article is used as bait for those organisms.

16 Claims, 3 Drawing Sheets a = Foam Layer
b = Adhesive + Additives a = Foam Layer
b = Adhesive + Additives

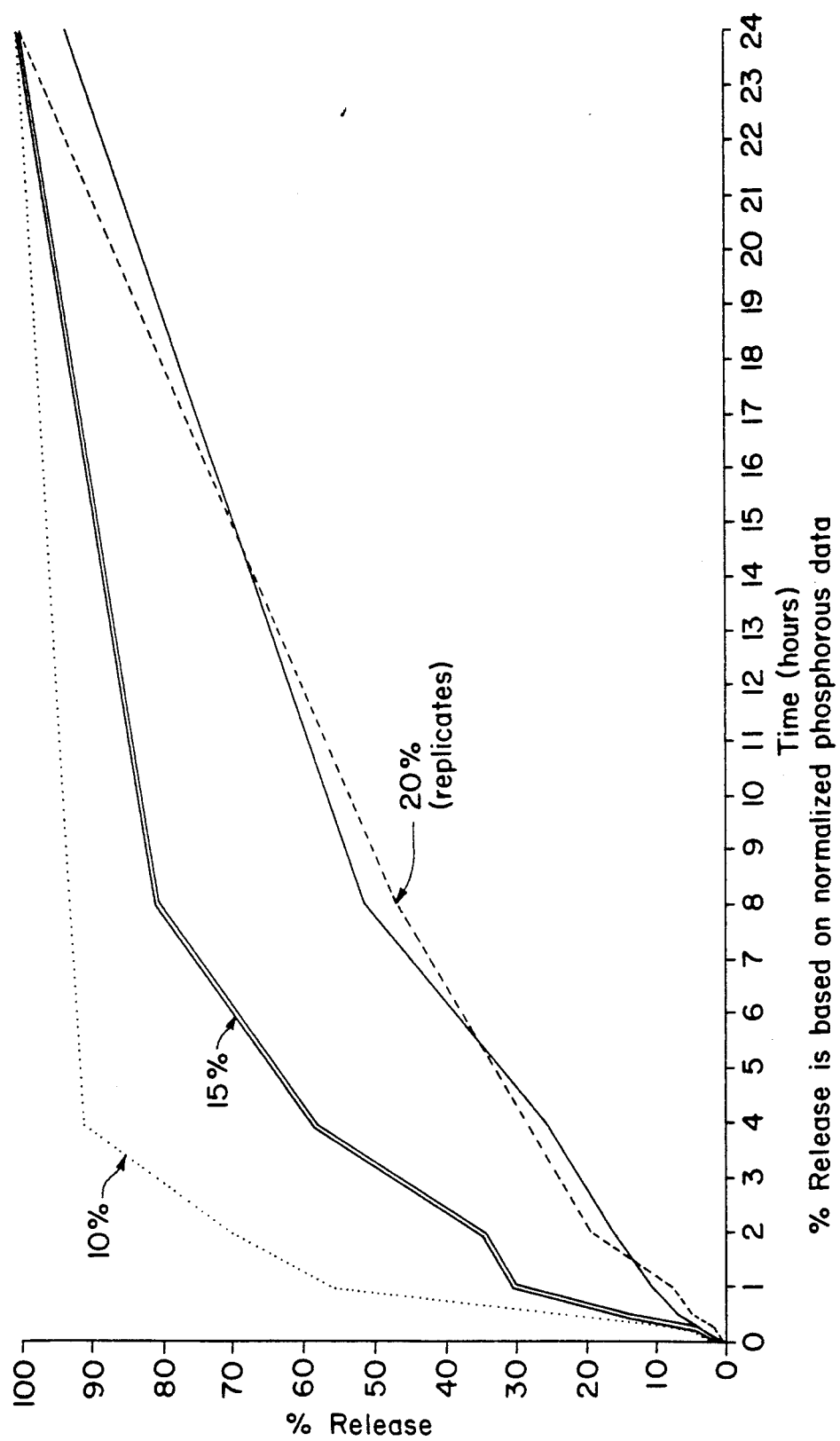

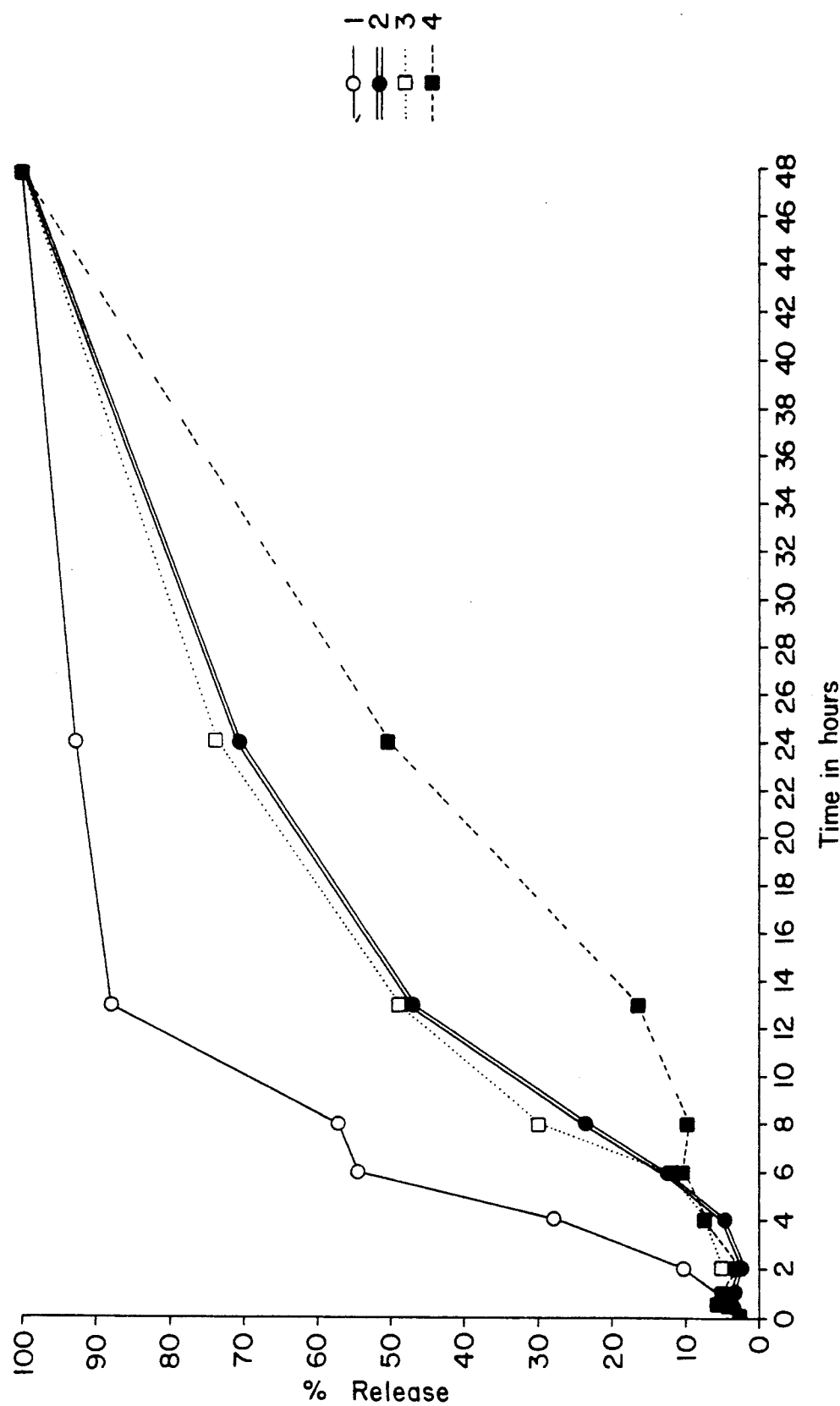

DEGRADABLE ARTICLES AND METHODS OF USING SUCH ARTICLES AS DEGRADABLE BAIT

FIELD OF THE INVENTION

The invention relates to articles which are capable of degrading in the environment surrounding the article, as well as capable of releasing additives at a sustained rate into that environment. The invention also relates to the method of using those articles as degradable artificial bait for aquatic or marine organisms such as fish.

BACKGROUND OF THE INVENTION

Articles prepared from degradable materials are becoming increasingly important in view of findings that certain materials, such as plastics, remain intact over long periods of time. In the environment, articles made from materials that do not degrade sufficiently are having conspicuously harmful and deleterious effects. For the ocean environment in particular, it has been recently noted that even small, virtually non-degradable articles such as plastic artificial fishing worms used to bait a recreational fisherman's hooks have been found intact in the oceans and digestive tracts of marine mammals. Given artificial bait's popularity among recreational fishermen, and as discussed below, given the commercial fishermen's increasing need for artificial baits, a degradable version of the article would be strongly desirable.

Artificial fishing bait has become especially popular with all types of fishermen. For instance, recreational fishermen find this type of bait attractive because it is easy to store in a tackle box and it avoids the sometimes distasteful chore of handling and using natural bait such as worms or squid. However, recreational fishing represents just a small portion of fishing activity. Commercial fishing activity represents the larger portion of the fishing market and could benefit from an artificial bait in various ways.

For instance, artificial bait could be stored for long fishing expeditions without worrying about the refrigeration normally required for natural bait. The bait, which can be delivered in dry form, weighs much less than natural bait. It is anticipated that a ton of natural bait can be replaced by a couple hundred pounds of the degradable bait. Similar savings on volume are also possible. In addition, if made in sheet form, the bait could be delivered to and stored in commercial fishing vessels in rolls, for ease of handling. Even further, with the advent of automatic baiting for commercial longline fishing vessels, such rolls can be more safely incorporated into a baiting procedure so that the bait is cut and attached to hooks as the bait sheet unwinds from the roll.

Using this type of bait would be likely to reduce accidents which sometimes occur when using automatic baiting of natural bait. Specifically, natural bait does not always have a uniform size nor is it always in a shape that is easily hooked. As a result, using natural bait requires that someone continuously feed the bait operation and manually place the bait in the slicer of the automatic baiter. This activity sometimes leads to the accidental cutting or hooking of hands or fingers. On the other hand, sheets of artificial bait can be cut to a uniform size and fed to the hooks of the baiting equipment in a manner such that little manual handling is required.

Moreover, artificial bait can be more durable. Natural bait begins to lose its integrity after a period of time in the water and bait can be lost by falling off the hook, or by sea gulls and small fish tearing the bait off the hook. If designed properly, artificial bait can remain on the line for logger periods of time and made strong enough so that it is not easily removed by tearing. In the end, such durability will likely result in larger catch yields.

However, as has been shown, the drawback to the artificial baits on the market today is that they do not possess sufficient degradability. For instance, various bait constructions presently use poly(vinyl chloride), lead jigs and other plastic materials. All of these are believed to be essentially non-degradable materials. See U.S. Pat. Nos. 4,731,247 issued to Wolford et al., Mar. 15, 1988 (cellulose ether and plasticizers); 4,666,717 issued to Smith et al., May 19, 1987 (polyamines and copolymers of ethylene and ethylenically unsaturated monomers); 3,684,519 issued to Combs, Aug. 15, 1972 (polyacrylamide and monomers); and PCT Application 87/07476 (polyurethane foams). As an example, artificial baits such as the well-known plastic worms are prepared from poly(vinyl chloride) and have been known to remain intact for many years. As recently reported, such plastic worms are being found in the digestive tracts of sea otters. Thus, the harmful effects of using such articles are just beginning to manifest themselves, and if commercial fishermen are forced to look for alternatives to natural bait, a degradable artificial alternative would certainly be desired. Likewise, other industries and markets would benefit from degradable articles.

Various degradable materials which might be adapted for use as a degradable bait are known. For example, U.S. Pat. No. 4,132,839, issued to Moran et al. Jan. 2, 1979, discloses prepolymers which, when foamed, provide biodegradable hydrophilic polyurethane foams. The question of how or whether such foams might be incorporated in a degradable bait which is palatable to fish and with sustained release capabilities is not addressed. A bait which can release an attractant in a controlled manner has been proposed in U.S. Pat. No. 4,245,520, issued to Carr Jan. 20, 1981. Its formulation produced a gel which must be refrigerated or frozen. U.S. Pat. No. 4,463,018, issued to Carr Jul. 31, 1984, used gelatin, agar, locust bean gum, partially hydrolyzed cellulose, sorbic acid, and humectants such as glycerol, thus producing a material having improved heat stability and shelf life at the expense of palatability to fish.

Another reference, U.S. Pat. No. 3,410,689, issued to Nathan Nov. 12, 1968, discloses a polyurethane foam mixed with an attractant as a bait which "disjoins," or breaks into relatively large pieces upon immersion in water. This bait relies on the break-up of the article to distribute the attractant.

SUMMARY OF THE INVENTION

It is an object of the invention to provide a novel degradable, yet durable, article which sufficiently degrades over an environmentally acceptable period of time, wherein the article comprises a degradable polyurethane polymer foam or gel and wherein the polymer has hydrolytically labile ester linkages.

It is also an object to provide a degradable article comprising functional additives in an amount sufficient to be released from the article at a sustained rate.

It is also an object to provide a novel degradable bait for aquatic or marine organisms wherein the bait comprises
  (a) at least one layer of a degradable polyurethane polymer where the polymer has hydrolytically labile ester linkages and
  (b) sensory stimulant additives which are releasable from the bait at a sustained rate sufficient to attract aquatic or marine organisms.

It is also an object to provide a novel method of attracting aquatic or marine organisms wherein the method comprises using the degradable bait described above.

Those of ordinary skill in the art would recognize that sensory stimulant additives might function as repellents as well as attractants. Such persons would also appreciate that the articles described herein and their method of manufacture can be varied by methods known to those with skill in the art. Thus the invention is limited only by the claims, and is not to be confined to the embodiments and examples disclosed in this application.

Furthermore, although this invention is conveniently described in terms of bait for fish, it should be noted that an article which is shown to be degradable in water need not be used in water. For example, the article may be used as an insect attractant or repellant in air and then, perhaps, disposed of in a landfill. Also, other aggressive environments such as compost piles, activated sewage sludge, or those containing detergent enzymes, extremes of pH or living tissues are contemplated as being suitable to degrade the article.

BRIEF DESCRIPTION OF THE DRAWINGS

FIGS. 2 and 3 show the percentage of additive release over time from different preferred embodiments of the invention.

DETAILED DESCRIPTION OF THE INVENTION

Figure 1:
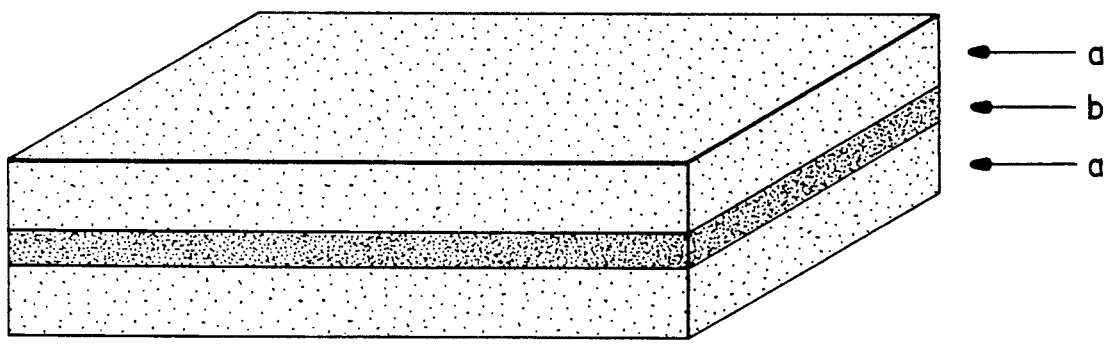
FIG. 1 shows a cross-section of a preferred embodiment of a degradable bait for aquatic or marine organisms.

The present invention uses polyurethane foam and gel fabrication technology to assemble one or more layers of polyurethane, reinforcing scrim, and adhesives or coatings into sheets, shapes or rolls with characteristics controlled for proper release of sensory stimulants. The stimulants are introduced either during the curing operation or after the polyurethane has been cured. The polyurethane material is formulated so that it will be storage stable when dry and, preferably, will swell when wet into a flesh-like consistency that has adequate strength for up to about three days, but which will degrade nd disappear after prolonged exposure to water, preferably within one year or less. In one of the preferred embodiments, a degradable isocyanate-capped prepolymer having lactate moieties present for easy enzymolysis and hydrolysis, is formed optionally into a thin sheet, using an approximately equal amount of an aqueous solution of surfactant, such as a silicone surfactant, that will give a relatively hydrophobic foam. The sheet is cast onto a moving belt, and a strength reinforcing paper or scrim such as cheesecloth may be laid down at the same time so that the scrim becomes positioned near the center of the sheet. The sheet is then immersed in a solution of attractants; e.g., a mixture of selected amino acids, either with or without drying of the sheet between casting and impregnation. In this operation, because of the hydrophobic nature of the surfactant, it is preferable to compress the sheet as it enters the attractant solution in order to express air bubbles and to allow saturation. The reason for the use of the hydrophobic surfactant is that it will be difficult to rewet the bait sheet during use, thus prolonging the release of the water-soluble chemosensory attractants. When this procedure is used to prepare sheets which are approximately 15% by weight of attractants, the rate of release upon rewetting is such that about half of the attractant material is released within one to eight hours, depending on the amount of agitation.

The degradability of the novel article depends on the presence of hydrolytically labile ester linkages in the polyurethane foam. Those linkages can be introduced to the polymer structure of the foam by using a polyol which has been reacted with an $\alpha$-hydroxy carboxylic acid. The polyol can be used in well-known "one shot" and "prepolymer" methods for preparing foams.

Generally, an $\alpha$-hydroxy carboxylic acid is heated under reflux with a polyol. The acid and hydroxyl groups condense to form the desired hydrolytically labile ester linkages. Optionally, the resulting hydroxyester polyol is mixed with another polyether or polyol. The polyol or polyol blend is usually dewatered in order to eliminate possible side reactions in the subsequent steps. In the "one-shot" method, the polyol or polyol blend is mixed with an isocyanate, near stoichiometric amounts of water, catalysts, and possibly other additives, and foams immediately. In the "prepolymer" method the polyol or polyol blend is capped with an isocyanate. The isocyanate-capped hydroxyester polyether polyol, or prepolymer, will foam upon the addition of water.

As used herein "degradability" of the article in an environment, means the ease of or the article's susceptibility to losing its physical integrity, i.e., breaking down into small particle form. For instance, in terms of an article used in a marine or aquatic environment, degradability means the ease of or susceptibility to losing its physical integrity over time under the conditions found in such environments, e.g., saline environment. It is also postulated that to achieve ultimate degradability, the particles resulting from the breakdown described above should be susceptible to further decomposition wherein the particles are consumed by ubiquitous environmental microbial agents.

Another aspect of degradability as it applies to baits is its effect on the target organisms. If an item is degradable, there is the potential for the item to change too much in character, or to release materials which interfere with the action of the sensory stimulants included in the bait. The degradable article would ideally be composed of a neutral carrier with reasonably durable physical characteristics, which allows the sensory stimulants to be released, and then degrades without counteracting its original purpose.

The hydroxy carboxylic acid, which is used to impart degradability to the article, need not be the sole carboxylic acid used to react with the polyol. Other acids, such as adipic acid, may be mixed with the hydroxy carboxylic acid to produce a degradable article. The use of a mixed-acid component will affect the ultimate physical characteristics of the article, including its rate of degradation.

Suitable $\alpha$-hydroxy carboxylic acids used to react with the polyol and impart degradability are, preferably, lactic and glycolic acids. These are more preferred because they are very labile, and also cheap and readily available. Other higher molecular weight α-hydroxy acids such as the propionic, butyric, and isobutyric homologs are usable in this invention. The higher molecular weight acids have a lower reactivity during polymer synthesis. If a higher molecular weight acid is used, some sort of catalyst or accelerator might be used during the esterification step.

The polyols used to react with the aliphatic hydroxy carboxylic acid are from one of two polyol systems. The two systems are (1) low molecular weight aliphatic or substituted aliphatic alcohols containing from 2 to 8 hydroxyl groups per molecule, and (2) polyether or polyester polymeric polyols, or a mixture of the systems. Using a mixture of various polyols may be advisable to adjust the final article characteristics such as rate of degradation, texture, density and rate of release of the attractant and wettability of the article.

Suitable low molecular weight alcohols of the first polyol system have 2 to 8 hydroxyl groups and a molecular weight of less than about 1000 and preferably 500 or less. Specific alcohols include, but are not limited to, butanediol, hexanediol, glycerol, 1,2,3-butanetriol, 1,2,4-butanetriol, trimethylolethane, trimethylolpropane, erythritol, pentaerythritol, adonitol, arabitol, mannitol, sorbitol, iditol, dulcitol, sucrose, dipentaerythritol, triethanolamine and condensation products of ethylene and propylene oxides with ethylene diamine, diethylene triamine; and triethylene tetramine.

The polyether polyols of the second system preferably are essentially linear, have a molecular weight not exceeding about 4000, and most preferably not exceeding about 2000. Suitable polyethers are prepared by homopolymerization of ethylene oxide, or propylene oxide, and include random copolymers and block copolymers such as polyoxyethylene diol capped with polyoxypropylene chains and polyoxypropylene diols capped with polyoxyethylene. Suitable linear polyethers may also be prepared by condensing an alkylene oxide of 4 carbons or less (e.g., ethylene, propylene or tetramethylene oxide) with a low molecular weight polyhydroxylic alcohol such as those described above. In such condensation products the polyether chains are essentially linear and have an average molecular weight of from 50 up to about 4000. Commercially available polyether polyols include CARBOWAX 600, 1000 and 1450 (from Union Carbide Chemicals and Plastics Co., Danbury, Conn.).

Suitable linear polyester polymeric diols include those such as the Formrez 66 series (1,6-hexanediol adipates of molecular weight 500–3000) or the Formrez-II series (Diethylene glycol adipates of molecular weight 500–3000) (supplied by Witco Chemical Corporation, New York, N.Y.).

Useful polyester and polyether polymeric triols include those having a molecular weight of about 1000 to 10,000, preferably 3,000–7,000. Commercially available polyether polyols include, for example, TPEG 990, an ethylene oxide-based triol having a nominal molecular weight of 990 (from Union Carbide).

The hydroxy ester resulting from the mixture of the α-carboxylic acid and the polyols may be further combined with any of the above listed polyols or a mixture thereof. The further addition of the polyols may be used to fine-tune degradability and other desirable traits of the final article.

The polyol and the hydroxy acids are reacted together under conditions well known for preparing such condensation products. See U.S. Pat. No. 4,049,592 issued to Marans et al. Sep. 20, 1977. The following illustrates several ways the polyol systems can be used to prepare the condensation products containing the labile ester linkages.

A. A low molecular weight alcohol and sufficient hydroxyacid are combined to form a condensation reaction product. The hydroxy acid should be reacted with the alcohol in amounts sufficient to completely esterify. The preferably trifunctional, hydroxyacid ester condensation product serves as a crosslinking agent for a linear polyether polyol (e.g., polyoxyethylene glycol) system by providing branching units. In addition, it imparts degradability to the foam which ultimately results. The hydroxy acid ester is also employed in amounts sufficient to provide the desired properties, i.e., if it is desired to increase rigidity, solvent resistance and other properties associated with crosslink density, the amount of crosslinking agent is increased.

B. Linear polyether and polyester polyols completely esterified with hydroxy acid (preferably lactic acid) and blended with the low molecular weight alcohol can be used.

C. A polyester or polyether polymeric triol condensed with an α-hydroxy acid, may be used.

D. The hydroxy acid ester condensation product formed in A above can be condensed with ethylene or propylene oxides to form essentially linear polyether chains originating with the hydroxy groups of the ester. Such chains would have the molecular weight distribution as described above for the linear and triol polyethers. This system may be exemplified by the trimethylolpropane (or ethane) ester formed by condensation with lactic acid followed by further condensation of the hydroxyl groups of the ester (3 per mole) with ethylene oxide to provide polyols having three essentially linear polyether chains per mole.

As mentioned above, the polyols (or polyol blend) are next capped with a polyisocyanate to make a liquid prepolymer.

The polyisocyanates suitable for capping the polyols include polyisocyanates such as the polyaryl polyisocyanate described in U.S. Pat. No. 2,683,730, toluene diisocyanate ("TDI"), triphenylmethane-4,4',4",-triisocyanate, benzene-1,3,5-triisocyanate, hexamethylene diisocyanate, xylene diisocyanate, isophorone diisocyanate, chlorophenylene diisocyanate, diphenylmethane-4,4'-diisocyanate, naphthalene-1,5-diisocyanate, xylene-alpha, 3,3'-dimethyl-4,4'-biphenylene diisocyanate, 2,2',5,5'-tetramethyl-4,4'-biphenylene diisocyanate, 4,4'-methylenebis (phenylisocyanate), 4,4'-sulfonylbis (phenylisocyanate), ethylene diisocyanate, trimethylene-diisocyanate and the like. TDI is most preferable. Mixtures of any one or more of the above-mentioned organic isocyanates may be used as desired. The polyisocyanates or mixtures thereof which are especially suitable are those which are commercially available, have a high degree of reactivity and a relatively low cost, e.g., TDI. Thus, the aromatic isocyanates are preferred. However, if greater hydrolytic and color retention stability are desired, aliphatic and cycloaliphatic diisocyanates are preferred.

Capping is preferably effected by using an excess of isocyanate to insure complete capping of the polyol. Thus, the ratio of isocyanate groups to the hydroxyl groups used for capping is between about 1.8 to about 4 isocyanate to hydroxyl, and preferably about 2.1 to about 3 isocyanate to hydroxyl molar ratio. In order to achieve a crosslinked network formation on foaming, the reactive components may be formulated in a variety of ways. For example, when water is the sole reactant with the isocyanate groups leading to chain growth during the foaming process, the isocyanate-capped reaction product preferably has an average isocyanate functionality from about 2 and up to about 6 or more depending upon the composition of the polyol and capping agent components. When the isocyanate capped reaction product has an isocyanate functionality of only about two, then the aqueous reactant may contain a dissolved or dispersed isocyanate-reactive crosslinking agent having an effective functionality greater than two. In this case, the reactive crosslinking agent is reacted with the capped resin when admixed during and after the foaming process has been initiated. When the isocyanate capped resin has an isocyanate functionality of only about two, then a polyisocyanate crosslinking agent having an isocyanate functionality great than two may be incorporated therein, either preformed or formed in situ, and the resultant mixture may then be reacted with the aqueous reactant, optionally containing dissolved or dispersed isocyanate-reactive crosslinking agent leading to a crosslinked, infinite network hydrophilic polyurethane foam.

As indicated above, when the first linear polyol containing system is used, a crosslinking agent is preferably used. Those agents not only include the low molecular weight alcohols which have been reacted with the hydroxy acid, but also include the unreacted low molecular weight alcohols as well as other water soluble or water dispersible crosslinking agents can be used. The agents should be polyfunctional and reactive with isocyanate groups. Agents other than the low molecular weight alcohols listed earlier include, but are not limited to, materials such as diethylenetriamine, triethylenetetramine, tetraethylenepentamine, polyethyleneimine, toluene-2,4,6-triamine, ethylenediamine, aminoethanol, trimethylenediamine, tetramethylenediamine, pentamethylenediamine, hexamethylenediamine, ethanolamine, diethanolamine, hydrazine, benzene-1,2,4-tricarboxylic acid, nitrilotriacetic acid, citric acid, 4,4'-methylenebis (o-chloroaniline), and the like. The water soluble or water dispersible crosslinking agents chosen are those which cause a crosslinked network to form during or after the foaming process begins to take place. When using the triol containing polyol system, or some linear diol systems, a crosslinking agent may not be required.

In the alternative a diol-based material or a mixture having an overall functionality of about two or less can be converted into a suitably strong foam material by heating with excess isocyanate sufficient to allow formation of allophanates or other by-products of the isocyanate reaction.

The Aqueous Component

To effect foaming and preparation of the crosslinked degradable polymer network, the component including the hydroxyester polyol or polyol blend is simply combined with an aqueous component.

When water is added to the polymer in either the one-shot or prepolymer method, other ingredients may be included with the water. Potential additives include catalysts and surfactants or cell structure control agents which regulate the size, density, and degree of openness of the foam cell structure. That is, they control such properties as texture, slipperiness and density of the final article. Such commercially available surfactants include as Hamposyl-O ®, (an oleate sarcosine (from W. R. Grace & Co.-Conn., Lexington, Mass.), Brij 72 ® (from ICI Americas, Bloomington, Del.) and others known to those of ordinary skill in the art. Further additives may be used to control the surface texture or "feel." For example Polyox ®, a high molecular weight (5–10 million) polyethylene glycol (from Union Carbide), may be used to impart a slippery feel. Similar results may be obtained with Carbopol, a polyacrylic acid polymer (from Union Carbide). Generally, pigments, dyes and colorants, as well as anti-mold agents such as polysorbates, may be added at this stage.

Control of foam structure is one convenient method to control the rate of release of the sensory attractants. It has been observed that a foam having small cells that have a multiplicity of cell windows in place (i.e., a high content of partly closed cells) releases a stimulant more slowly than a foam having an open cell, largely reticulated structure.

The way in which addition of water influences the foams obtained can be illustrated by the following water index value:

$$\text{Water Index value} = \frac{\text{equivalents of H}_2\text{O}}{\text{equivalents of NCO}} \times 100$$

Thus, because one-half mole of water is equal to one equivalent of isocyanate, where 0.5 mole $H_2O$ is used with 1 eq. NCO, the water index value is 100.

An index of 100 indicates that both equivalents are equal or "balanced". An Index of 95 indicates that there is a 5% deficiency of water. A slight theoretical excess of isocyanate, usually 3–5%, is common practice in the prior art, particularly with flexible foams made by the one-shot method mentioned above and described in more detail below.

Using the prepolymer method and water in amounts from about $H_2O$ Index Value of 100 up to about $H_2O$ Index Value of 200, poor foaming results unless materials such as surfactants or the like are included. Amounts up to about $H_2O$ Index Value of 200 require a catalyst. When using a $H_2O$ Index Value of about 78,000, surprisingly good foams result which improve in characteristics with added amounts of molar water. Thus, the available water content in the aqueous reactant is from about an $H_2O$ Index Value of about 1300 to about 78,000 and desirably from about 4,000 to about 40,000.

"Available water" in the aqueous reactant is that water accessible for reaction with the prepolymer, and which is exclusive of water which may form a layer during reaction, or supplemental water which may be necessary because of additives present in the forming the aqueous reactant.

Because large amounts of water are in the aqueous reactant during reaction, i.e., the present system is not dependent upon a molar NCO-water type reaction, it is possible to combine a great variety of materials in the aqueous reactant which are otherwise not possible with limited water reacting systems.

The aqueous reactant may be used at temperatures from about 2° C. to about 100° C. as desired.

Although the prepolymer is easily foamed by the above process, it is also possible to add, although not necessary, supplemental foaming materials such as those well known to the artificial sponge foaming art.

After foaming has been effected, the foam may be dried, if desired, under vacuum from 1 to 760 Torr at a temperature of about 0° to about 150° C. If the foams are to be in sterile environments, the foams may be heat or chemically sterilized prior to use.

An alternative to the prepolymer method described above is the well-known "one shot" method of preparing a polyurethane foam. Instead of reacting the hydroxyester polyol or polyol blends with the isocyanates prior to the addition of water, the polyols, isocyanates, and water are reacted simultaneously. When using the one shot method, catalysts such as tin salts, iron salts or the like are required to promote the chain extension reaction of the polyols' hydroxyl groups. Other catalysts, such as tertiary amines, are used to promote the evolution of $CO_2$ as a result of the reaction of water and isocyanates.

Although this invention is described in terms of producing a foamed article, non-foamed articles can be produced and are within the scope of the invention. A foamed article is produced when (1) the hydroxyester polyol or polyol blend is mixed with isocyanate and water or (2) the isocyanate capped hydroxyester polyol or polyol blend is mixed with water. The hydroxyl groups from the water and the isocyanate groups react with the evolution of $CO_2$ and consequent foaming. If polyamines, low molecular weight alcohols or polyols and the like are substituted for the water, $CO_2$ does not evolve, and foaming does not occur. The product is an elastomeric gel instead of a foam.

Sensory Stimulant Additives

The additives which can be used in the degradable articles are varied and depend upon the article being made and the intended use of the article. The additives used herein should be releasable at a sustained rate from the article. By "sustained rate," it is meant that the sensory stimulant additive is released gradually from the article over a period of time. Control of foam structure and the method used to incorporate the sensory stimulant into the article as well as the physical location of the stimulant in the article are ways to control the rate of sensory stimulant release. For example, a foam structure having a large relative number of small, closed cells would tend to exhibit a slower release rate. Similarly, a more hydrophobic foam would tend to release the sensory stimulants more slowly, as would a foam in which the sensory stimulant had been incorporated as part of the foam structure itself. Other additives incorporated in the foam may affect the release rate, as well. The type of surfactant used, if any, may play an important role in rate of attractant release. In this context, nontoxic and biodegradable surfactants would be especially preferred. Surfactants which may be considered as examples in this connection are HAMPOSYL® 0 and HAMPOSYL® 1-30 (from W. R. Grace & Co.-Conn.; TRITON® CG-110 SURFACTANT (from Rohm and Haas Company, Philadelphia, Pa.); DOW CORNING® 190 SURFACTANT (from Dow Corning Corp., Midland, Mich.); SANDOTERIC® TFL and SANDOPAN® DTC Linear Gel (from Sandoz Chemicals Corp, Charlotte, N.C.), PLURONIC® F-87, F-108, and F-127 PRILL® and PLURONIC® L62 (from BASF Corporation Chemicals Division, Parsipanny, N.J.). The additives could be incorporated within the interior of the foam or some other structure of the article, thus resulting in a prolonged sustained release of the additives. On the other hand, the additives can be coated on the surface of the foam or the surfaces of other structures of the article. This would likely result in a quick sustained release. The thickness of the article itself affects the release of the additives, with thicker articles usually exhibiting a slower release of additives.

The additives can be incorporated by immersing the foam in a solution of additive components and allowing the foam to imbibe the additives. Another method includes adding the additives in the aqueous component used in the above-mentioned polyurethane foaming methods. Thus, when the crosslinked foam structure is formed, the additives become encapsulated within the structure's interstices. This method would be especially preferable when the additives are in water insoluble form. In a preferred method, the additives are incorporated between layers of degradable foam.

Degradable Fish Bait

As described above, one use of the degradable article is in the field of artificial bait for fish and other marine organisms. This embodiment of the degradable article uses the polyurethane foam and/or gel fabrication technology described above and comprises at least one layer of the degradable polyurethane polymers described earlier. The bait also comprises sensory stimulant additives which are present in an amount and which are releasable from the bait at a sustained rate sufficient to attract the fish or other aquatic or marine organisms and incite them to ingest the bait article.

One preferred structure of the bait employs a "sandwich" structure of preferably two additive-containing degradable foam layers which are adhered together by a degradable polymer adhesive. The process for constructing the bait is described below in terms of making the sandwich-type embodiment, but the process employs well-known foam-forming and foam lamination techniques which can be easily modified to fabricate other constructions as well.

For instance, a prepolymer containing the hydrolytically labile ester linkages described earlier and an aqueous component are reacted to form a thin sheet of polyurethane foam which is cast onto a release surface or a moving belt. Optionally, the foam is cast in the shape of a large bun or log, and then sliced with a saw or hot wire, etc., into sheet form. The sheet is then optionally dried before being immersed in a solution of sensory stimulant additives. To maximize the absorption and distribution of additives, it may be preferable to compress the foam sheets before or after they enter the additive solution in order to express air bubbles.

Preferably, two unimbibed foam sheets are then laminated and adhered together preferably by a degradable polymer adhesive, and preferably an adhesive prepared from the same degradable polyurethane polymer used to make the foam and the desired sensory stimulants described below. Well-known adhesive formulation techniques may be used to form a paste from the polymer and stimulants. The resulting paste is then applied to one or both layers of the degradable foam. The adhesive is then cured using water (liquid or vapor) or other well known isocyanate reactive curing agents, including polyols, polyamines and the like. Optionally, the resulting laminate can be further coated with a degradable material, which is also preferably a material comprising the same degradable polymers. FIG. 1 illustrates a cross section of the sandwich-type structure with 1 and 2 representing the two polyurethane layers and 3 representing the adhesive.

With most baits, it will be preferable to construct the bait so that the thickness of the bait as a whole is in the range of 0.2 cm to 1.0 cm. However, other size baits might be required for certain species of aquatic animals.

As discussed below, the thickness is not limited to a particular range and will depend on the release rate as well as the shape and texture of bait desired. Likewise, the thickness of the adhesive layer can vary and will depend on the same factors. As discussed below, sensory stimulant additives may also be added to the adhesive layer and will affect the thickness of that layer.

In addition to having the adhesive layer and two foam layers, the above sandwich construction can also have an additional layer for reinforcement of the bait structure. Such a layer enhances the strength of the bait structure and facilitates the retention of the bait on a bait hook. The layer would be especially preferable when used to bait hooks on an automatic baiter. When used, the reinforcement layer is preferably placed in between the two foam layers and laminated or adhered thereto. In an alternative embodiment, the reinforcing layer is placed in the foam forming mixture during foaming so that when the foam forms, it forms around the reinforcing layer, thus encapsulating the layer. The reinforcing layer may be varied in terms of coarseness and type of material used in order to achieve the degree of strength desired. The reinforcing layer is preferably a degradable material such as cheesecloth, tobacco cloth, paper, cellulosic wovens or non-wovens, or rayon.

It should be appreciated that because foams and gels can be easily molded, the degradable bait can be in forms other than sandwich-type sheet described above. Using the appropriate molds, reinforcing layers and other additives, the construction can be in the form and color of natural bait such as frogs, minnows, worms or the like.

The sensory stimulant additives or attractants in the baits can be those well-known in the art. The additives can be olfactory and gustatory stimulants such as liquified or powdered fish or other marine products, fish oils, anise, amino acids or known synthetic liquid or solid attractants.

Additives which are in solid form include comminuted squid, shrimp, bunker or waste fish or parts normally disposed of during fish processing operations, e.g., fish heads, carcasses, etc. See U.S. Pat. No. 4,731,247 to Woolford et al.

In addition, additives can be prepared following the procedure or disclosure in Ed. Hara, *Chemoreception in Fishes*, Elsevier Scientific Publishing Co., New York (1982).

The additives must be present in the bait in an amount and must be released at a sustained rate sufficient to attract the species desired. As used herein "sustained rate" means the gradual release into the target organism's environment over a period of time. An additive is "gradually released" when it takes longer to release from the article than if it were simply dumped into the environment. See U.S. Pat. No. 4,731,247 to Woolford et al. The amounts and rates vary for the myriad of species, for some of which exemplary rates are described below.

For sport or recreational fishing for species such as bluefish, rockfish, etc., the release period is rather short, e.g., 15 minutes to two hours; and the bait should be designed to effectively release the additives over that time period. To achieve such release rates, the following features of the bait should be considered:

(1) additives imbibed at the surface of the bait article,
(2) large amount of additives,
(3) when additives are imbibed in one of the foam layers, the foam should be open-celled and preferably free of skin layer and cut in thin layers, and
(4) use of coatings and impregnants, instead of the foam, for the release site of the additives, and
(5) use of foams with an open pore structure.

In commercial fishing for species such as haddock, salmon, cod, torsk and tuna, the release period should be longer, e.g., over 1 to 20 hour period or longer. For lobster baits, the release period should preferably be from 3 to 5 days. To achieve those periods of release, the following features of the bait should be considered:

(1) thorough saturation of the bait article with additives,
(2) encapsulated solid or liquid additives, e.g., comminuted fish scraps and oils;
(3) adhesive layer which contains attractant additives,
(4) foam density or heavy skin layers,
(5) when the foam layers are imbibed with additives, use of thick foam layers, and
(6) a more closed pore structure.

As mentioned above, using the above-described article as an artificial bait for fish is just one embodiment of the degradable article, and other uses can be envisioned as well. Degradable articles with the capability of sustained release of additives would be useful for surgical implants and pharmaceuticals, wound dressings and medicaments, personal care items such as diapers and the like. To accommodate each of the above uses, the release of the additives would be controlled and designed in a similar fashion to the controlled release of the sensory stimulating additives of the fish bait. For some applications, the additives may be contained in particles, or other defined shapes, as opposed to layers.

The following examples are provided to illustrate the invention and should not be interpreted as limiting the scope thereof or the claims which follow the examples.

I PREPOLYMERS

Example 1

A mixture of 336.8 g (2.5 moles) of trimethylolpropane and 1399 g (13.7 moles) of 88% lactic acid were heated under reflux for six hours at 115° C., then 15 hours at 135° C. under reduced pressure (2 Torr.) until no more volatiles could be removed. The hydroxyl content of the product was 6.43 meq/g. A degradable prepolymer was then made by first dewatering a mixture of 770 g (0.77 mole) of CARBOWAX 1000, 45 g (0.5 mole) of butanediol, and 166.2 g (0.5 mole) of the lactated trimethylolpropane prepared above for two hours at 100° C. and 1 Torr., then adding 600 g (3.45 mole) of toluene diisocyanate and maintaining the temperature at 70° C. for one hour. The isocyanate content of the product was 2.68 meq/g and the viscosity at 25° C. was 29,900 cp.

Sheets of foam were made by mixing 30 g of the prepolymer from Example 1 with 30 g of a 2% (by weight) aqueous solution of Dow Corning silicone surfactant DC-190 and pouring the foaming mixture between two polyethylene sheets (9 inches wide). The sheets were then immediately pulled between two cylindrical metal bars spaced 35 mils apart. Before pouring the foaming polymer a single layer of environmentally degradable cotton cheesecloth was placed between the polyethylene films. After a few minutes, the polyurethane sheets had cured to foams, with the cheesecloth engulfed and secured near the center of the foam sheet. The polyethylene sheets were then removed. The foam sheets had expanded to approximately 110 mils and had density of 0.12 g/cc (7.1 lb/cu.ft.).

A piece of the above-described sheet weighing approximately 0.1 g was kept in 100 ml of a 0.75% aqueous solution of Terg-A-Zyme ® enzyme (from Alconox, Inc., New York, N.Y.) at 80° C. until the foam disintegrated, leaving nothing but the cheesecloth. This required 4–5 days. Several pieces of conventional urethane foam (produced by Armalay Sponge Co., Walled Lake, Mich. and Vining Industries, Springfield, Ohio) did not disintegrate after more than three weeks under the same conditions.

Examples 2–8

The following examples indicated in Table I below illustrate additional examples using CARBOWAX 1000, butanediol, lactated trimethylolpropane (TMP), as well as other polyols. The prepolymers disclosed below were prepared under the same conditions as those described above in Example 1. These prepolymers were then used to prepare foams in a manner described in Example 1, except a cheesecloth was not used.

isocyanate content of the product was 2.60 meq/g and the viscosity was 16,700 cp at 25° C.

Example 10

The purpose of this example is to illustrate the reaction of a poly(oxyethylene) triol with lactic acid to form a lactated triol, and to illustrate the reaction of this triol with a diisocyanate; in this case, TDI. This differs from previous examples of lactated prepolymers in that the previous examples used a high molecular weight diol and a low molecular weight triol. In this example, the triol had a nominal molecular weight of 990.

Reaction with Lactic Acid

A mixture of TPEG 990 (300 g, 0.303 mole), an ethylene oxide-based triol with nominal molecular weight of 990 from Union Carbide, and 196.2 g (1.85 moles) of 85% lactic acid was heated to 200° C. over a period of 13 hours in order to form the lactate ester. During this time, 44 g of water was distilled from the mixture. The product was dewatered for an additional four hours at 160°–198° C. and 1–2 Torr., causing removal of an additional 12 g of volatile materials. The dried lactate product was found to have a water content of less than 0.1%.

A mixture of 300 g of the lactate product and 142.8 g (0.82 mole) of OLIN TYPE 2 ® TDI from The Olin Corp., Stamford, Conn.) was heated at 70° C. for eight hours. During the last two hours, the isocyanate content of the reaction product remained constant at 2.15

TABLE I

| Example Number | Starting Materials (Mole) | | | | | | | | Typical Foam Density g/cc |
|---|---|---|---|---|---|---|---|---|---|
| | CARBOWAX 1000(a) | PEG 600(b) | Butanediol | Triol(c) | Lactated TMP(d) | TDI(e) | NCO(f) | Viscosity(g) | |
| 2 | 1.00 | — | — | — | 0.382 | 3.83 | 2.46 (2.44) | 15,000 | 0.07 |
| 3 | 0.25 | 0.15 | — | — | 0.188 | 1.72 | 2.56 (2.41) | 13,600 | 0.07 |
| 4 | 0.25 | — | 0.25 | — | 0.188 | 1.72 | 3.29 (2.88) | 16,400 | 0.06 |
| 5 | 0.385 | — | 0.25 | — | 0.188 | 1.72 | 2.50 (2.88) | 57,450 | 0.09 |
| 6 | 0.77 | — | 0.45 | — | 0.376 | 3.44 | 2.76 (2.88) | 11,000 | 0.09 |
| 7 | 0.50 | — | — | 0.008 | 0.188 | 1.91 | 2.51 (2.58) | 4,850 | 0.08 |
| 8 | 1.00 | — | — | 0.016 | 0.376 | 3.56 | 2.29 (2.30) | 4,680 | 0.08 |

(a)a polyoxyethylene glycol having a molecular weight of about 1000 from Union Carbide.
(b)a polyoxyethylene glycol having a molecular weight of about 600 from Union Carbide.
(c)random triol copolymer of 75% ethylene oxide and 25% propyleneoxide having a molecular weight of about 7000.
(d)prepared as in Example 1.
(e)toluene diisocyanate.
(f)millequivalence of isocyanate functionality per gram of prepolymer.
(g)centipoise as measured at 25° C.

Example 9

A mixture of 225 g (2.5 moles) of 1,4-butanediol and 950 g (9 moles) of 85% lactic acid was heated under reflux for 2.5 hours (106°–109° C.). Then, water and excess lactic acid were removed by distillation at atmospheric pressure as the temperature was raised gradually to 200° C. over a period of 11.5 hours. A total of 275 ml of volatile material was removed. The pressure was then reduced to 1–2 Torr. and the temperature was maintained at 132°–141° C. for an additional 4.5 hours, causing distillation of a further 44 ml of volatile material. The non-volatile product weighed 853 g. The hydroxyl content of the product was indicating that the butanediol lactate product was 66% pure.

A mixture of 500 g CARBOWAX 1000 (0.5 mole), 22.3 g (0.17 mole) trimethylolpropane, and 117 g the butanediol lactate prepared above was dewatered two hours at 110° C. and 1–2 Torr. To this was added 431 g (2.47 moles) of tolylene diisocyanate and the temperature was maintained near 70° C. for five hours. The meq./g. The product, or prepolymer, had viscosity at 25° C. of 35,000 cp.

A sheet was made essentially as described in Example 1 using 50 g of the prepolymer and 50 g of water. When dried, the sheet had a density of 0.15 g/cc and water capacity of 9 grams per gram. It disintegrated in a boiling phosphate buffer solution in 110 minutes.

Example 1

"Fully Lactated" Prepolymer

A mixture of 1540 g (1.54 moles) of CARBOWAX ® 1000, 103.2 g (0.77 mole) of trimethylolpropane, and 1030 g (9.27 moles) of 85% lactic acid was heated to 200° C. during two hours, causing the distillation of 234 g of water. The temperature was maintained at 200° C. for an additional 4½ hours. The total amount of water removed was 260 g. Following this, unreacted lactic acid and other volatile materials were removed under reduced pressure at 200° C. and approximately 1 Torr. until distillation stopped. This required two hours and the total amount of distillate was 194 g. The lactated polyol product that remained undistilled weighed 2227 g. A determination of hydroxyl content indicated a value of 2.3 meq/g.

To 700 g of the lactated polyol product was added 307 g of TDI. This mixture was allowed to react at 70° C. for seven hours, after which time the isocyanate content was found to be 1.82 meq/g and the viscosity at ambient temperature was 92,000 cp.

A sheet, 0.1 inch thick, was made from equal weights of the isocyanate-capped prepolymer and water as described in Example 1. Pieces of this sheet were found to fragment into fine powder after 3–4 hours in a 2% aqueous solution of dibasic sodium phosphate at 90°–100° C.

Example 12

Example of Prepolymer Composed Only of Lactated Diols and Diisocyanate, with Strength Obtained Through Allophanate Formation A mixture of 770 g (0.77 mol) of CARBOWAX® 1000, 40.9 g (0.385 mole) of diethylene glycol, and 515 g (4.86 moles) of 85% lactic acid was heated to 200° C. and maintained at this temperature for an additional half hour, causing removal of 122 g of water. The unreacted lactic acid and other volatiles were removed by distillation at approximately 1 Torr. at 200° C. The water content of the product lactated diols thus was reduced to less than 0.05% by weight. To 700 g of the lactated polyols was added 301.1 g of TDI and the resulting mixture was allowed to react for four hours at 70° C. The resulting isocyanate-capped prepolymer had viscosity of 90,500 cp and isocyanate content of 1.51 meq/g. It was formed into a sheet, using equal weights of prepolymer and water, according to the procedure described in Example 1. Pieces of this sheet, in a 2% aqueous solution of dibasic sodium phosphate at 90°–100° C., were reduced to fine powder in one hour.

Example 13

Synthesis of Prepolymer Using a Mixture of Acids

A mixture of 350.7 g (2.4 moles) of adipic acid, 63.3 g (0.6 mole) of 85% lactic acid, 254.7 g (2.4 moles) of diethylene glycol, and 26.8 g (0.2 mole) of trimethylolpropane was heated at atmospheric pressure for eight hours as the temperature was raised gradually to 233° C. until no more water was evolved. The hydroxyl content of the polyester triol product was 1.24 meq/g, indicating an equivalent weight of 806.

Preparation of Foam Sheet

Forty-six grams of the polyester triol product was mixed with 1.5 g of water, 0.7 g of stannous octoate, and 0.9 g of Union Carbide silicone surfactant L-520®. To this mixture was added 10.9 g of TDI. The mixture was stirred vigorously for 70 seconds and the resulting froth was poured between two polyethylene films with dimensions of approximately 9 inches by 13 inches, and the assembly was passed between two cylindrical bars spaced 1/16 inch apart in order to spread the froth into a sheet of uniform thickness. After two hours, the polyethylene film was stripped from the polyurethane sheet, which was found to be fine-celled and to have a density of 0.24 g/cc.

Preparation of Laminated Bait

Twenty-three grams of the polyester triol was mixed with 15 g of a powdered fish attractant, 0.75 g of water, 0.35 g of stannous octoate, and 0.45 g of silicone L-520. One-half of this paste (12.3 g) was stirred quickly with 2.73 g of TDI, and 2.1 g of this reacting adhesive composition was used to adhere two strips of the polyurethane sheet which weighed 2.37 g each. The following day the laminate was found to weigh 6.98 g, indicating that it contained 15% by weight of the solid attractant powder. A second laminated strip made in a similar way was found to contain 21% by weight of the attractant.

Extraction of Bait Composition

A three-gram portion of the laminate having 21% by weight of solid attractant encapsulated in the central laminating adhesive was shaken at moderate speed on a rotary shaker for one week at 18° C. with 400 ml of water. Samples were removed periodically for analysis of phosphorous, a component of the attractant mixture, as a means of estimating the amount of attractant that had been extracted. After two hours, 25% as much phosphorous had been extracted as was extracted during the entire week. After 24 hours, 73% of the extractable phosphorous had been removed, on the same basis. The total amount of phosphorous extracted in one week was nearly the amount calculated to have been present, indicating that nearly all of the attractant had been extracted. Furthermore, the extracted bait sheet, after drying, had lost 18% of its weight but had not changed significantly in appearance.

Degradability of the Bait

A piece of the foamed polyurethane sheet weighing 1.25 g, was placed into a stirred solution of 4.7 g of $Na_2HPO_4$ in 250 ml of water (pH 9.1) which was kept at 95°–100° C. The sheet disintegrated into a very fine white powder within 15 minutes. A similar piece of the laminated product of Example 10 was tested in the same way. It delaminated in six minutes, broke into many large scraps within 10–15 minutes, and formed fine powder within 110 minutes. The longer survival time appeared to be due to the dense adhesive layer which resisted hydrolysis to a greater degree than the foam.

Example 14

Non-foamed Articles

Synthesis of Elastomer

The following examples in Table II below illustrate non-foamed polyurethane elastomers or gels made according to the invention described herein. The degradable prepolymer of Example 1 was reacted with varying proportions of a trifunctional polyethylene glycol of nominal molecular weight 990 ("TPEG 990") and polyethylene glycol of nominal molecular weight 400 ("PEG" 400) (both available from Union Carbide). The mixture was degassed under vacuum and poured into ⅜" inner diameter vinyl tubing, and allowed to cure at about 100° C. for two hours.

TABLE II

| | Composition of Various Elastomers | | |
|---|---|---|---|
| Run | Degradable Prepolymer | TPEG 990 | PEG 400 |
| a | 7.0 g (17.6 meq NCO) | 5.8 g (17.6 meq OH) | 0 |
| b | 7.0 g (17.6 meq NCO) | 4.6 g (14.1 meq OH) | 0.70 g (3.5 meq OH) |
| c | 7.0 g (17.6 meq NCO) | 3.48 g (10.5 meq OH) | 1.41.g (7.1 meq OH) |
| d | 7.0 g (17.6 meq NCO) | 2.32 g (7.0 meq OH) | 2.1 g (10.6 meq OH) |
| e | 7.0 g (17.6 meq OH) | 1.16 g (3.5 meq OH) | 2.81 g (14.1 meq OH) |

TABLE II-continued

Composition of Various Elastomers

| Run | Degradable Prepolymer | TPEG 990 | PEG 400 |
|---|---|---|---|
| f | 7.0 g (17.6 meq NCO) | 0.58 g (1.8 meq OH) | 3.16 g (15.8 meq OH) |

The elastomers were found to be increasingly soft as the amount of trifunctional material (TPEG 990) was reduced.

The elastomers were also prepared from using glycerol as the crosslinking agent. The formulations using glycerol (from J. T. Baker, Phillipsburgh, Pa.) contained PEG 400 and a curing catalyst, DABCO ® triethylene diamine (from Air Products, Allentown, Pa). The addition of DABCO ® catalyst allowed the polymer to be cured at room temperature.

The following proportions (Table III) were used to make the elastomers containing glycerol.

TABLE III

| Run | Degradable Prepolymer | Glycerol | PEG 400 | DABCO |
|---|---|---|---|---|
| a | 7.0 g (17.6 meq NCO) | 0.054 g (1.76 meq OH) | 3.16 g | 0.01 g |
| b | 7.0 g (17.6 meq NCO) | 0.1078 g (3.52 meq OH) | 2.81 g | 0.01 g |
| c | 7.0 g (17.6 meq NCO) | 0.1616 g (5.28 meq OH) | 2.46 g | 0.01 g |
| d | 7.0 g (17.6 meq NCO) | 0.2155 g (7.04 meq OH) | 2.11 g | 0.01 g |
| e | 7.0 g (17.6 meq NCO) | 0.2694 g (8.8 meq OH) | 1.76 g | 0.01 g |

The elastomers were increasingly stiff as the level of glycerol increased. At 10% glycerol, the material was slightly tacky, but even this material was stronger than the typical plasticized poly(vinyl chloride) bait "worms." This latter elastomer lost its physical integrity on soaking in deionized water for five days without stirring. It liquified and settled to the bottom of the container.

Preparation of Attractant Loaded Gels

A fish-attractant mixture (0.6 g) was dissolved in 20 g of deionized water. To this solution 4.0 g of gel prepolymer, was added and mixed for 45 seconds. The liquid reaction mixture was then poured into an aluminum foil mold containing cheesecloth and allowed to gel. The gels could also be prepared without cheesecloth, which is used to provide strength. The following samples were tested.

TABLE IV

Compositions of Various Gels Containing Attractants

| Run | Prepolymer | Attractant | water | % Prepolymer |
|---|---|---|---|---|
| a | 2.0 g | 0.30 g | 20.0 g | 10 |
| b | 3.0 g | 0.45 g | 20.0 g | 15 |
| c | 4.0 g | 0.60 g | 20.0 g | 20 |

Release Rates

Samples were assayed for attractant release by placing them in a measured amount of deionized water (400 g) and gently agitating on an orbital shaker at 18° C. Aliquots of water were taken out at specific time intervals and release was calculated by monitoring the phosphorous concentration resulting from release of attractants. FIG. 2 shows the release of attractants (based on phosphorous analysis) of containing various attractants. As the prepolymer concentration decreases in a gel, the crosslinked density also decreases. The release rate of attractant increases as the crosslink density decreases.

DEGRADABILITY OF FOAMS

Example 15

Three methods were used to compare the degradation rate of the various foams.

a. 100 mg of the foam was kept in 100 ml of a 0.75% aqueous solution of Terg-A-Zyme enzyme (from Alconox, Inc.) at 80° C. until the foam disintegrated into small particles. A foam prepared according to the method in Example 1 completely disintegrated leaving the cheesecloth. This required 4–5 days. Several pieces of conventional urethane foam (produced by Armalay Co. or Vining Industries) did not disintegrate after more than three weeks under the same conditions.

b. In this method three foams were made by mixing 40 g of the prepolymer from Example 9 with 40 ml of 3 different 2% aqueous solution of surfactants. The three surfactants used were BASF's Pluronic L-62 and Pluronic F-68 surfactants, and Dow-Corning's DC-190 surfactant. The resulting three foams possessed medium sized, coarse, and fine cells, respectively, and all three were flexible. The foams were individually stirred in a 2% basic sodium phosphate solution (pH 9.1) at 90°–100° C. until the foam disintegrated through a combination of hydrolytic and mechanical action. The coarse-celled foam made with F-68 surfactant survived 32 minutes; the medium-celled foam made with L-62 surfactant survived for 145 minutes, and the fine-celled foam made with DC-190 surfactant survived for 130 minutes.

The foam of Example 10 disintegrated in 110 minutes. Pieces of the foam from Example 11 were found to fragment into fine powder after 3–4 hours.

The foamed polyurethane sheet of Example 13 disintegrated into a very fine white powder within 15 minutes; a similar piece of the laminated bait delaminated in six minutes, broke into many large scraps within 10 to 15 minutes, and formed fine white powder within 110 minutes.

By contrast, a nondegradable foam made in a similar manner from W. R. Grace & Co.-Conn.'s HYPOL ® 2000 polyurethane prepolymer and a 2% aqueous solution of PLURONIC ® L-62 surfactant survived in the same test for 23–24 hours.

c. In this method the hydrolytic degradation of various foams was carried out in a pH of ocean water) weak buffer (10 mm phosphate buffer) at 90° C. 750 mg of the foam was suspended in 200 ml of the buffer at 90° C. A very gentle rotational stirring was introduced so as not to cause a mechanical degradation. This may be considered as an accelerated test for hydrolytic degradation in the marine water (except that microbes were absent). The time required for the foams to fall apart into small particles were compared. After disintegration, the particles settled to the bottom of the solution. The degradable foam of Example 9 (using DC-190 surfactant) fell apart into small particles in 3–4 hours. Commercial polyurethane foams like Scottfoam ®

(900Z) (Knoll International Holdings, Inc. Addystone, Pa.) and General Foam ® (6400L773) (from General Foam, West Parsippany, N.J.) degraded in 22 days and 13 days, respectively. Both of the commercial foams are polyester urethanes derived from adipic acid, diethylene glycol and TDI.

Sustained Release Rates

Example 16

A mixture of powdered synthetic sensory additives was comminuted in a mortar and pestle. A three gram sample of this powder was dissolved in 100 ml of water, which was then soaked into an approximately ⅛ inch sheet of the foam illustrated in Example 1. The sample piece of foam weighed 16.9 g. The sheet was immersed until it contained 15% by weight of attractants and then dried. Seven pieces of this sheet product weighing a total of 1.4 g each were stirred with 100-ml portions of water at moderate speed with a magnetic stirring bar. The water was filtered and evaporated to recover the attractants. After 10, 30 and 120 minutes, the samples had released 71%, 82% and 90%, respectively, by weight of the total amount that was recovered at the end of the experiment by squeezing the foam.

In an experiment similar to the one above, a phosphorus-containing compound was added to the additive mixture to provide phosphorous for analysis by inductively-coupled plasma elemental analysis (ICP) instrument Model 3410, (from Fissons-ARL, Valencia, Calif.). Samples were shaken in a jar to measure the rate of release. After 30 and 120 minutes, the foam had released about 57% and 79% of the available phosphorous. The foam had released nearly all of its load between 4 and 6 hours. When small pieces of the additive-containing foam were put into an aquarium with pinfish or with sea bass, they were readily consumed by the fish.

Encapsulation of Solid Chemosensory Attractants

Example 17

The prepolymer of Example 1 was diluted to 80% concentration (W/W) by mixing 27.6 g of the prepolymer with 6.9 g of methyl ethyl ketone. To 7.7 g of the 80% solution was added 1.93 g of a phosphorous-containing chemoattractant solid mixture similar to Example 16. A paste of the mixture was then made by mixing. Then 1.2 g of this paste was applied on the degradable urethane foam sheet of Example 3 having approximately 0.31 cm thickness and 0.6 g weight. A second sheet of the same foam of a similar dimension and weight was placed on the paste and the two sheets stuck together overnight on the bench top so that moisture (humidity) curing took place while the solid chemosensory attractants were thereby encapsulated in the center of the laminate. Other baits were prepared in a similar manner. Table V describes various configurations of baits.

TABLE V

| CONFIGURATION OF VARIOUS ARTIFICIAL BAITS | | | |
|---|---|---|---|
| Bait Number | Foam Thickness (Mils) | Weight Ratio Foam/Paste | Other Additives |
| 1 | 75 | 1:1 | None |
| 2 | 150 | 1:1 | None |
| 3 | 150 | 1:1 | Polyox ® |
| 4 | 150 | 2:1 | None |

Endnotes:
(a) Bait thickness is approximately twice the thickness of the foam.
(b) Paste contains 20% by weight chemosensory attractants and 64% by weight degradable prepolymer and 16% methyl ethyl ketone.

Additional Sustained Release Rates

Example 18

Four bait samples prepared according to Example 17 were introduced into a bottle containing 400 ml deionized water. The baits were prepared in a sandwich-type structure similar to the bait described in Example 13. The bottle was then gently agitated on an orbital shaker at 18°±1° C. Aliquots of water (5 ml) were taken at different intervals and assayed for phosphorous using inductively coupled plasma (ICP). FIG. 3 illustrates the release profile of phosphorous from various samples reported in Table V.

What is claimed is:

1. A degradable bait for aquatic or marine organisms wherein the bait comprises
    (a) a first layer of a degradable polyurethane polymer wherein the polymer has hydrolytically labile ester linkages formed from reaction of a polyol with an α-hydroxy carboxylic acid;
    (b) a second layer of a degradable polyurethane polymer wherein the polymer has hydrolytically labile ester linkages formed from reaction of a polyol with an α-hydroxy carboxylic acid;
    (c) an adhesive layer between said first and second layers of degradable polyurethane polymer, said adhesive layer comprising sensory stimulant additives in an amount effective for release from the bait in an aqueous medium at a sustained rate sufficient to attract aquatic or marine organisms.

2. A degradable bait according to claim 1 wherein the layers are adhered together by a degradable adhesive.

3. A degradable bait according to claim 2 wherein the adhesive is a polyurethane polymer which has hydrolytically labile ester linkages.

4. A degradable bait according to claim 2 wherein the polyurethane polymer and the polymer adhesive comprise the same polymer.

5. A degradable bait according to claim 4 wherein the polyurethane polymer foam and the polymer adhesive are prepared from a prepolymer which is the reaction product of
    (a) a condensation product from one or more polyols selected from the group comprising
        (i) monomeric low molecular weight aliphatic alcohols having from 2 to 8 hydroxyl groups per molecule; and
        (ii) essentially linear polyether or polyester polymeric polyols; and an alpha hydroxy carboxylic acid, and
    (b) a polyisocyanate.

6. A degradable bait according to claim 5 wherein the condensation product is the reaction product of trimethylolpropane and lactic acid.

7. A degradable bait according to claim 1 wherein the bait in addition comprises a reinforcing layer.

8. A degradable bait according to claim 7 wherein the polyurethane polymer layers and the reinforcing layer are laminated together such that at least one reinforcing layer is between the polymer layers.

9. A method of attracting aquatic or marine organisms comprising placing in the vicinity of said aquatic or marine organisms a degradable bait comprising
   (a) a first layer of a degradable polyurethane polymer wherein the polymer has hydrolytically labile ester linkages formed from reaction of a polyol with an α-hydroxy carboxylic acid;
   (b) a second layer of a degradable polyurethane polymer wherein the polymer has hydrolytically labile ester linkages formed from reaction of a polyol with an α-hydroxy carboxylic acid;
   (c) an adhesive layer between said first and second layers of degradable polyurethane polymer, said adhesive layer comprising sensory stimulant additives in an amount effective for release from the bait in an aqueous medium at a sustained rate sufficient to attract aquatic or marine organisms.

10. A method according to claim 9 wherein the bait comprises a degradable adhesive.

11. A method according to claim 10 wherein the adhesive is a polyurethane polymer which has hydrolytically labile ester linkages.

12. A method according to claim 10 wherein the degradable polymer and the adhesive comprise the same polymer.

13. A method according to claim 12 wherein the degradable polymer and the polymer adhesive are prepared from a prepolymer which is the reaction product of
   (a) a condensation product from one or more polyols selected from the group comprising
      (i) monomeric low molecular weight aliphatic alcohols having from 2 to 8 hydroxyl groups per molecule;
      (ii) essentially linear polyether or polyester polymeric polyols; and an alpha hydroxy carboxylic acid, and
   (b) a polyisocyanate.

14. A method according to claim 13 wherein the condensation product is the reaction product of trimethylolpropane and lactic acid.

15. A method according to claim 9 wherein the bait in addition comprises a reinforcing layer.

16. A method according to claim 15 wherein the degradable polymer layers and the reinforcing layer are laminated together such that at least one reinforcing layer is between the polymer layers.

* * * * *